United States Patent
Kanehiro et al.

(10) Patent No.: US 11,026,932 B2
(45) Date of Patent: Jun. 8, 2021

(54) MEDICINAL COMPOSITION FOR PREVENTING OR TREATING INFLAMMATORY RESPIRATORY DISEASE

(71) Applicant: NATIONAL UNIVERSITY CORPORATION OKAYAMA UNIVERSITY, Okayama (JP)

(72) Inventors: Arihiko Kanehiro, Okayama (JP); Utako Fujii, Okayama (JP); Daisuke Morichika, Okayama (JP); Naohiro Oda, Okayama (JP); Nobuaki Miyahara, Okayama (JP); Akihiko Taniguchi, Okayama (JP); Hiroki Kakuta, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 454 days.

(21) Appl. No.: 15/772,901

(22) PCT Filed: Sep. 9, 2016

(86) PCT No.: PCT/JP2016/076554
§ 371 (c)(1),
(2) Date: May 2, 2018

(87) PCT Pub. No.: WO2017/043616
PCT Pub. Date: Mar. 16, 2017

(65) Prior Publication Data
US 2020/0179353 A1 Jun. 11, 2020

(30) Foreign Application Priority Data
Sep. 10, 2015 (JP) .............................. JP2015-178885

(51) Int. Cl.
A61K 31/44 (2006.01)
A61P 11/06 (2006.01)
A61P 11/08 (2006.01)
A61K 31/4184 (2006.01)
A61K 31/4192 (2006.01)

(52) U.S. Cl.
CPC .......... *A61K 31/44* (2013.01); *A61K 31/4184* (2013.01); *A61K 31/4192* (2013.01); *A61P 11/06* (2018.01); *A61P 11/08* (2018.01)

(58) Field of Classification Search
CPC .................................................... A61K 31/44
See application file for complete search history.

(56) References Cited

U.S. PATENT DOCUMENTS

| | | | |
|---|---|---|---|
| 6,479,670 B1 | 11/2002 | Belloni et al. | |
| 6,794,416 B2 | 9/2004 | Belloni | |
| 2005/0148590 A1 | 7/2005 | Tsang et al. | |
| 2010/0120742 A1 | 5/2010 | Kakuta et al. | |

FOREIGN PATENT DOCUMENTS

| | | |
|---|---|---|
| JP | 2003-507465 A | 2/2003 |
| JP | 2007-517037 A | 6/2007 |
| JP | 2010-111588 A | 5/2010 |
| JP | 2013-177329 A | 9/2013 |
| JP | 2013177329 A * | 9/2013 |
| JP | 2014-076953 A | 5/2014 |
| WO | WO 00/61233 A2 | 10/2000 |
| WO | WO 2008/105386 A1 | 9/2008 |
| WO | WO 2010/041449 A1 | 4/2010 |

OTHER PUBLICATIONS

STN document No. 159:447865.*
Day et al., Retinoic Acid Inhibits Airway Smooth Muscle Cell Migration, American Journal of Respiratory Cell and Molecular Biology; New York vol. 34, Iss. 6, (Jun. 2006): 695-703.*
Stolk et al., Retinoid treatment of Emphysema in Patients on the Alpha-1 International Registry. The REPAIR study: study design, methodology and quality control of study assessments, Ther Adv Respir Dis, (2010) 4(6) 319-332.*
Yokoyama et al.: "Effect of Aerosolized Docosahexaenoic Acid in a Mouse Model of Atopic Asthma," International Archives of Allergy and Immunology, vol. 123, No. 4, Dec. 2000 (Dec. 2002), pp. 327-332, XP009511913, ISSN: 1018-2438 (6 pages).
Layton: "The use of isotretinoin in acne," Dermato-Endocrinology, vol. 1, No. 3, Jun. 30, 2009 (Jun. 30, 2009), pp. 162-169, XP055570032 (8 pages).

(Continued)

*Primary Examiner* — Svetlana M Ivanova
(74) *Attorney, Agent, or Firm* — Buchanan, Ingersoll & Rooney PC (57) ABSTRACT

A method for treating an inflammatory respiratory disease, comprising administering an effective amount of an RXR agonist represented by formula (1) or (2) as an active ingredient.

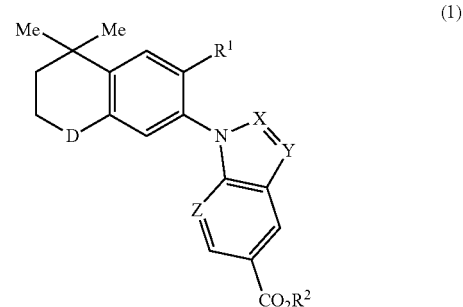

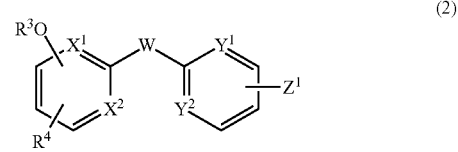

wherein D, $R^1$, $R^2$, X, Y, Z, $R^3$, $R^4$, $X^1$, $Y^1$, $X^2$, $Y^2$ and $Z^1$ are defined.

11 Claims, 5 Drawing Sheets

(56) References Cited

OTHER PUBLICATIONS

Dawson et al.: "The Retinoid X Receptors and Their Ligands," Biochimica et Biophysica Acta (BBA)—Molecular and Cell Biology of Lipids, vol. 1821, No. 1, Jan. 1, 2012 (Jan. 1, 2012), pp. 1-99, XP055570033, Amsterdam, NL, ISSN: 1388-1981 (99 pages).
Machine Translation of WO 2010/041449, published Apr. 15, 2010 (Japanese copy submitted May 2, 2018, (19 pages).
Machine Translation of JP 2013-177329, published Sep. 9, 2013 (Japanese copy submitted May 2, 2018, (28 pages).
Extended Search Report issued by the European Patent Office in corresponding European Patent Application No. 16844477.6-1109 dated Jul. 18, 2019 (12 pages).
International Search Report (PCT/ISA/210) dated Oct. 11, 2016, by the Japanese Patent Office as the International Searching Authority for International Application No. PCT/JP2016/076554.
Written Opinion (PCT/ISA/237) dated Oct. 11, 2016, by the Japanese Patent Office as the International Searching Authority for International Application No. PCT/JP2016/076554.

\* cited by examiner

Pathological lung tissue

MEDICINAL COMPOSITION FOR PREVENTING OR TREATING INFLAMMATORY RESPIRATORY DISEASE

TECHNICAL FIELD

The present invention relates to a medicinal composition for preventing or treating an inflammatory respiratory disease such as emphysema, bronchial asthma and pulmonary fibrosis, comprising an agonistic compound to a retinoid X receptor (RXR) (hereinafter, referred to as an "RXR agonist") as an active ingredient.

BACKGROUND ART

Emphysema is an irreversible disease in which infiltration by inflammatory cells such as neutrophils and alveolar macrophages is observed in a local site of a lung, leading to bronchiole fibrosis and alveolar rupture. Bronchial asthma is a chronic inflammatory disease of the airway characterized by increased airway hyperreactivity and airway constriction. Pulmonary fibrosis is a progressive refractory disease in which repair is abnormally enhanced in an alveolar epithelium disorder, leading to pulmonary interstitium fibrosis.

Pathophysiology of airway inflammation, emphysema formation and fibrosis in emphysema, bronchial asthma and pulmonary fibrosis has not been clearly understood.

Although emphysema is treated with a bronchodilator such as inhaled long-acting anticholinergic agent and inhaled long-acting β2 stimulator, it is just symptomatic treatment, and treatment agents have not been established. Furthermore, there are still many refractory asthmas and deaths from asthma which are uncontrollable even by optimal treatment with an inhaled steroid drug and an inhaled long-acting β2 stimulator, a leukotriene receptor antagonist, an oral steroid drug or the like as long-term management for bronchial asthma. Furthermore, a treatment agent effective for pulmonary fibrosis remains to be developed.

Retinoid X receptor (RXR) is a nuclear receptor which is one of transcription factors regulating DNA transcription in a ligand dependent manner. RXR is involved in gene expression, and forms a homodimer or a heterodimer with another nuclear receptor such as peroxisome proliferator-activated receptor γ (PPAR-γ), hepatic X receptor (LXR), retinoid receptor (RAR), vitamin D receptor (VDR) and NR4 for exerting its action.

It has been reported that an RXR full agonist is effective for diabetes and inflammatory diseases in an animal study. There are, however, no reports regarding airway inflammation.

It has been reported that regulatory T cells may be induced by activating PPAR-γ and NR4. Therefore, it can be expected that the above RXR heterodimer can be activated by an RXR agonist, resulting in additive or synergistic effect.

It is interestingly known that activation of an RXR heterodimer by an RXR agonist varies, depending on the structure of the RXR agonist. Therefore, each RXR partial agonist may have different capability to activate an RXR heterodimer, and thus, efficacy of each compound must be studied.

It has been found that an RXR agonist, NEt-3IB reduces increase in triglyceride compared to a known RXR full agonist (see Patent Reference No. 1). The RXR agonist, NEt-3IB has the structural formula represented by formula (5).

The inventors have created an RXR-selective partial agonist as a novel RXR agonist without the side effects as described above (see, for example, Patent Reference Nos. 2 to 4).

CBt-PMN

CBTF-PMN

NEt-4IB

PRIOR ART REFERENCES

Patent References

Patent Reference No. 1: JP 2010-111588 A
Patent Reference No. 2: JP 2013-177329 A
Patent Reference No. 3: WO 2008/105386 A1
Patent Reference No. 4: JP 2014-076953 A

SUMMARY OF THE INVENTION

Problems to be Solved by the Invention

An objective of the present invention is to provide a medicinal composition comprising a compound capable of preventing or treating an inflammatory respiratory disease with a mechanism of action different from conventional method, as an active ingredient.

Means for Solving the Problems

After intense investigation to solve the above problems, the inventors have studied efficacy of various RXR agonists using various inflammatory respiratory disease models, to achieve this invention.

Specifically, the present invention relates to a medicinal composition for preventing or treating an inflammatory respiratory disease comprising an RXR agonist as an active ingredient.

Preferably, the medicinal composition comprises an RXR agonist as an active ingredient, which is a compound represented by Formula (1) or Formula (2):

(1)

wherein D is selected from $CMe_2$, N-methyl, N-ethyl or N-isopropyl;
$R^1$ is selected from a methyl group, a hydroxy group, a methoxy group or an ethoxy group;
$R^2$ is selected from H, a methyl group or an ethyl group;
X is selected from N, CH or C—$CF_3$;
Y and Z are selected from N or CH;

(2)

wherein $R^3$ is selected from the group consisting of an alkyl group, an alkenyl group, an alkynyl group and an aryl group which may be straight-chain or branched-chain, and unsubstituted or substituted;
$R^4$ is selected from the group consisting of an alkyl group, an alkenyl group, an alkynyl group, an aryl group and an alkoxy group which may be straight-chain or branched-chain and unsubstituted or substituted;
W is selected from $NR^5$ or $CR^5_2$;
$R^5$ is selected from hydrogen and an alkyl group, an alkenyl group, an alkynyl group and an aryl group which may be straight-chain or branched-chain and unsubstituted or substituted;

$X^1$ and $Y^1$ are selected from CH or N;
$X^2$ and $Y^2$ are selected from CH, $CR^6$ or N;
$R^6$ is selected from the group consisting of an alkyl group, an alkenyl group, an alkynyl group, an alkoxy group, a halogen, nitro group and an amino group which may be straight-chain or branched-chain and unsubstituted or substituted; and
$Z^1$ is selected from a carboxyl group, a carboxylate group or a hydroxamic group, bound directly or via a linker selected from the group consisting of an alkylene group, an alkenylene group and an alkynylene group.

Here, an active ingredient is preferably an RXR agonist which is a compound represented by Formula (1), particularly preferably an RXR agonist which is a compound represented by Formula (3).

(3)

wherein X is selected from N or C—$CF_3$.

An active ingredient is preferably an RXR agonist which is a compound represented by Formula (2), particularly preferably an RXR agonist which is a compound represented by Formula (4).

(4)

A preferable embodiment of the present invention is a medicinal composition for preventing or treating emphysema. Another preferable embodiment of the present invention is a medicinal composition for preventing or treating bronchial asthma.

Effects of the Invention

The present invention can provide means for preventing or treating inflammatory respiratory diseases including COPD (emphysema, chronic bronchitis); bronchial asthma; bronchial asthma-COPD complication syndrome; pulmonary fibrosis; eosinophilic granulomatosis with polyangiitis; cystic fibrosis; and acute upper respiratory inflammation such as acute bronchitis, acute adenoiditis, acute laryngitis, acute epiglottitis and acute tonsillitis.

MODES FOR CARRYING OUT THE INVENTION

A medicinal composition according to the present invention is a composition for preventing or treating an inflammatory respiratory disease comprising an RXR agonist as an active ingredient.

Preferably, the medicinal composition comprises an RXR agonist as an active ingredient, which is a compound represented by Formula (1) or Formula (2):

(1)

wherein D is selected from $CMe_2$, N-methyl, N-ethyl or N-isopropyl;

$R^1$ is selected from a methyl group, a hydroxy group, a methoxy group or an ethoxy group;

$R^2$ is selected from H, a methyl group or an ethyl group;

X is selected from N, CH or C—$CF_3$;

Y and Z are selected from N or CH;

(2)

wherein $R^3$ is selected from the group consisting of an alkyl group, an alkenyl group, an alkynyl group and an aryl group which may be straight-chain or branched-chain, and unsubstituted or substituted;

$R^4$ is selected from the group consisting of an alkyl group, an alkenyl group, an alkynyl group, an aryl group and an alkoxy group which may be straight-chain or branched-chain and unsubstituted or substituted;

W is selected from $NR^5$ or $CR^5_2$;

$R^5$ is selected from hydrogen and an alkyl group, an alkenyl group, an alkynyl group and an aryl group which may be straight-chain or branched-chain and unsubstituted or substituted;

$X^1$ and $Y^1$ are selected from CH or N;

$X^2$ and $Y^2$ are selected from CH, $CR^6$ or N;

$R^6$ is selected from the group consisting of an alkyl group, an alkenyl group, an alkynyl group, an alkoxy group, a halogen, nitro group and an amino group which may be straight-chain or branched-chain and unsubstituted or substituted; and

$Z^1$ is selected from a carboxyl group, a carboxylate group or a hydroxamic group, bound directly or via a linker selected from the group consisting of an alkylene group, an alkenylene group and an alkynylene group.

A composition comprising an RXR agonist which is a compound represented by Formula (3) or Formula (4) is more preferably. Herein, a compound represented by Formula (3), wherein X is N, is sometimes referred to as "CBt-PMN", and a compound represented by Formula (4) is sometimes referred to as "NEt-4IB".

(3)

wherein X is selected from N or C—$CF_3$.

(4)

In the present invention, the above compound can be also a pharmaceutically acceptable salt. If there can be isomers of any of the compounds or a salt thereof (for example, optical isomers, geometric isomers and tautomers), the present invention embraces these isomers, and also embraces solvates, hydrates, and various shapes of crystals.

In the present invention, pharmaceutically acceptable salts include pharmacologically and pharmaceutically acceptable common salts. The following are specific examples of such salts.

Examples of a base addition salt include alkali metal salts such as sodium salts and potassium salts; alkaline earth metal salts such as calcium salts and magnesium salts; ammonium salts; aliphatic amine salts such as trimethylamine salts, triethylamine salts, dicyclohexylamine salts, ethanolamine salts, diethanolamine salts, triethanolamine salts and procaine salts; aralkylamine salts such as N,N-dibenzylethylenediamine salts; heteroaromatic amine salts such as pyridine salts, picoline salts, quinoline salts and isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts and tetrabutylammonium salts; and basic amino acid salts such as arginine salts and lysine salts.

Examples of an acid addition salt include inorganic acid salts such as hydrochlorides, sulfates, nitrates, phosphates, carbonates, bicarbonates and perchlorates; organic acid salts such as acetates, propionates, lactates, maleates, fumarates, tartrates, malates, citrates and ascorbates; sulfonates such as methanesulfonates, isethionates, benzenesulfonates and p-toluenesulfonates; and acidic amino acid salts such as aspartates and glutamates.

The terms used herein, alone or in combination with another term, have the meanings below.

The term "alkyl group" means a straight-chain or branched-chain alkyl group having 1 to 20, preferably 1 to 10 carbon atoms; for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl and n-decyl groups. Preferred is an alkyl group having 1 to 6 carbon atoms such as methyl, ethyl group, n-propyl, isopropyl, n-butyl, isobutyl, sec-butyl, tert-butyl, n-pentyl, isopentyl, neopentyl, tert-pentyl, n-hexyl and isohexyl groups.

The term "alkenyl group" means a straight-chain or branched-chain alkenyl group having 2 to 20, preferably 2 to 8 carbon atoms in which the above "alkyl group" has one or more double bonds; for example, vinyl, 1-propenyl, 2-propenyl, 1-butenyl, 2-butenyl, 3-butenyl, 1,3-butadienyl and 3-methyl-2-butenyl groups.

The term "aryl group" means a monocyclic aromatic hydrocarbon group (phenyl group) and a polycyclic aromatic hydrocarbon group (for example, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl groups). Preferred is a phenyl or naphthyl group (1-naphthyl, 2-naphthyl group).

The term "alkynyl group" means an alkynyl group having 2 to 20, preferably 2 to 10 carbon atoms in which the above alkyl group contains one or more triple bonds; for example, ethynyl group, 1-propynyl, 2-propynyl, 1-butynyl, 2-butynyl and 3-butynyl groups.

The term "alkoxy group" means a straight-chain or branched-chain alkoxy group having 1 to 20 carbon atoms, including methoxy, ethoxy, propoxy, isopropoxy, butoxy, isobutoxy, sec-butoxy, tert-butoxy, pentyloxy, hexyloxy, octadecanoxy and allyloxy groups. Preferred is a straight-chain or branched-chain alkoxy having 1 to 6 carbon atoms.

The term "acyl group" means an alkanoyl group, an aroyl group and the like. The alkanoyl group includes alkanoyl groups containing an alkyl group having 1 to 6, preferably 1 to 4 carbon atoms (formyl, acetyl, trifluoroacetyl, propionyl and butyryl groups). The aroyl group includes aroyl groups containing 7 to 15 carbon atoms; specifically, benzoyl and naphthoyl groups.

In the present invention, the above compound has partial agonist activity to RXR. RXR is a nuclear receptor involved in DNA transcription, and thus the above compound can be referred to as a transcriptional regulatory compound. The term "regulation" or synonyms thereof as used herein must be interpreted as broad as possible, including enhancement or inhibition of action. Whether the above compound is an enhancer or inhibitor can be easily determined by a method as specifically described in Examples below.

There are no particular restrictions to a dosage when a pharmaceutical composition of the present invention is used. An appropriate dosage can be easily determined in any dosage regimen, for example, when action of a retinoid is regulated by combining the above compound, or when, without combining a retinoid-containing medicine, a drug of the present invention is administered for regulating action of retionic acid existing in a living organism. For example, for oral administration, an active ingredient can be used within a range of about 0.01 to 1000 mg per day for an adult. When a medicine containing a retinoid as an active ingredient is used in combination with a composition of the present invention, the composition of the present invention can be administered during, and/or either before or after administrating the retinoid.

As a medicine containing a composition of the present invention as an active ingredient, one or more substances selected from the above compounds can be administered directly, but can be preferably administered as an oral or parenteral pharmaceutical composition containing one or two or more of the compounds described above. An oral or parenteral pharmaceutical composition can be produced using formulation additives available for the person skilled in the art, that is, pharmacologically and pharmaceutically acceptable carriers. For example, one or two or more of the above compounds are added to a medicine effective for treating an inflammatory respiratory disease, that is, they can be used as a pharmaceutical composition in the form of so-called combination drug. Specifically, combination with an inhaled steroid, an inhaled long-acting β2 stimulator, a leukotriene receptor antagonist, an oral steroid drug or the like can be used.

A pharmaceutical composition suitable for oral administration can be, for example, tablet, capsule, powder, fine granules, granules, liquid and syrup. A pharmaceutical composition suitable for parenteral administration can be, for example, injection, infusion, suppository, inhalant, nasal drop, ointment, cream and patch. Pharmacologically and pharmaceutically acceptable carriers used for preparing the pharmaceutical composition include an excipient, a disintegrant or disintegration aid, a binder, a lubricant, a coating agent, a colorant, a diluent, a base, a dissolving agent or dissolution aid, a tonicity agent, a pH adjuster, a stabilizer, a propellant and an adhesive.

There will be specifically described various pharmacological actions of the composition according to the present invention and production processes therefor. Any compound contained in the composition of the present invention can be produced by appropriately modifying or changing starting materials, reagents and the reaction conditions used in the process for producing a compound as an active ingredient in the present invention. A process for producing a compound in the composition of the present invention is, however, not limited to those specifically illustrated in the following examples.

EXAMPLES

Example 1

<Preparation of Emphysema Mice and Evaluation of Drug Efficacy>

Emphysema mice were prepared in accordance with the following procedures described and used for evaluation of drug efficacy.

[Procedure 1]

Under anesthesia by pentobarbital or isoflurane administration, female BALB/c mice were intratracheally administered with swine pancreatic elastase to prepare (day 0) emphysema models.

[Procedure 2]

The mice were fed with a food containing CBt-PMN (the compound represented by Formula (3)) and NEt-4IB (the compound represented by Formula (4)) as RXR partial agonists from Day −4. Control mice were fed with a food containing bexarotene as an existing RXR full agonist.

[Procedure 3]

On Days 4 and 14, the mice underwent tracheotomy again under anesthesia by pentobarbital or xylazine-ketamine administration, followed by insertion of an endotracheal tube, and static lung compliance was measured using a respiratory function measuring equipment (Flexiware, SIREQ Inc.) for evaluating emphysematous alteration. Static lung compliance is an indication of extensibility of a lung tissue, and static lung compliance is increased in emphysema which is a disease associated with tissue destruction in an alveolar region.

[Procedure 4]

After the procedure 3, the mice were euthanized by exsanguination. After bronchoalveolar lavage, a lung tissue was removed for evaluating emphysema.

[Procedure 5]

In a group fed with a common food as an untreated group, emphysema was also induced for determining static lung compliance and evaluating emphysematous alteration.

[Procedure 6]

The data obtained was analyzed by Anova significance test, in which $p<0.05$ to an untreated non-emphysema group was indicated by "*". Furthermore, $P<0.05$ to an untreated emphysema group was indicated by "#".

Figure 1:
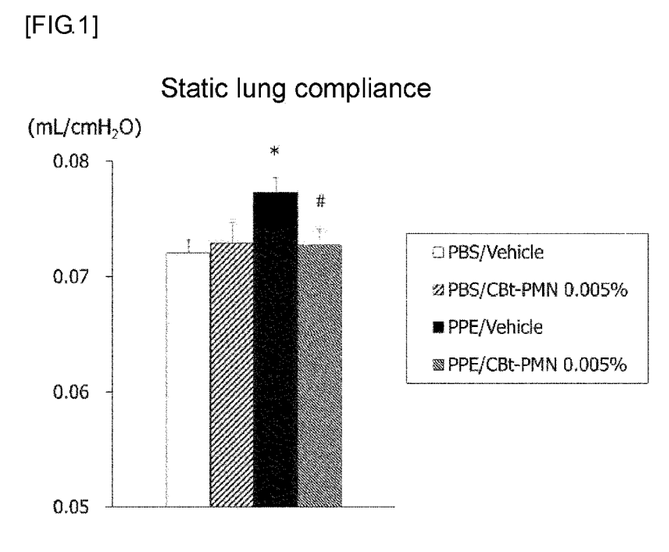
FIG. 1 is a graph for evaluating static lung compliance in emphysema model mice administered with CBt-PMN.
Figure 2:
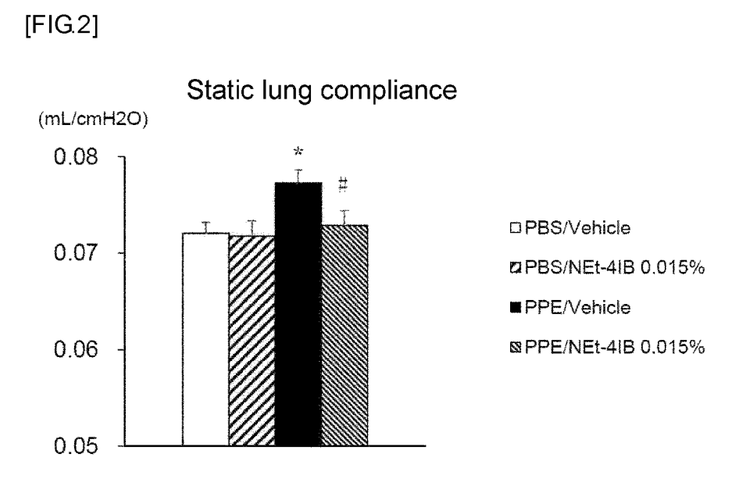
FIG. 2 is a graph for evaluating static lung compliance in emphysema model mice administered with NEt-4IB.

The results obtained are shown in FIGS. 1 to 6. FIG. 1 is a graph for evaluating static lung compliance in emphysema model mice administered with CBt-PMN. FIG. 2 is a graph for evaluating static lung compliance in emphysema model mice administered with NEt-4IB. Compared with the untreated group, significant improvement of static lung compliance was observed in the group administered with CBt-PMN or NEt-4IB as an RXR partial agonist. Improvement was slightly larger in the group administered with CBt-PMN than the group administered with NEt-4IB.

Figure 3:
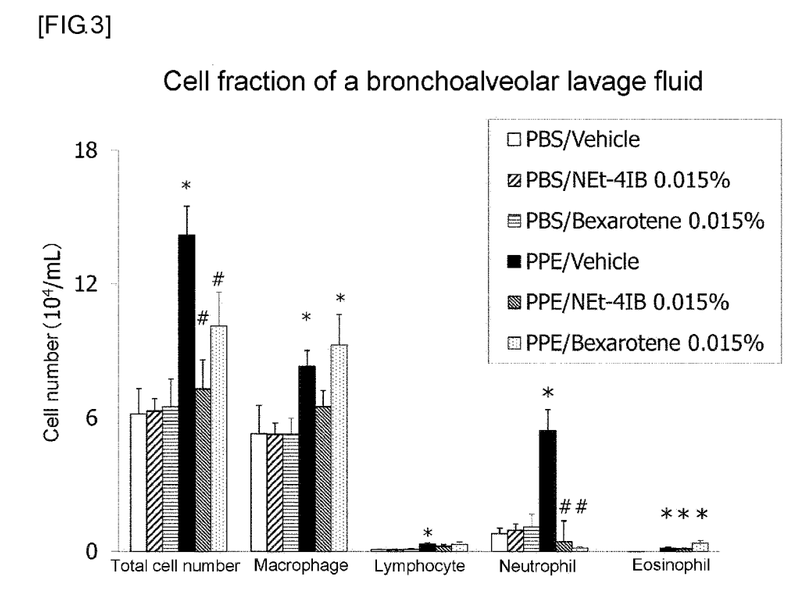
FIG. 3 is a graph of cell numbers in a cell fraction of a bronchoalveolar lavage fluid for emphysema model mice.

FIG. 3 is a graph of cell numbers in a cell fraction of a bronchoalveolar lavage fluid for emphysema model mice. For evaluating acute airway inflammation, the mice were administered with elastase and 4 days after the administration, underwent bronchoalveolar lavage under endotracheal intubation, and the cell fraction of the bronchoalveolar lavage was evaluated. Compared with the untreated group, reduction in a total cell number and a neutrophil number was observed in the group administered with the RXR partial agonist, NEt-4IB. The total cell number and macrophages were significantly reduced in the group administered with the RXR partial agonist, NEt-4IB in comparison with the drug non-administration group, and the effect was remarkably higher than the RXR full agonist, bexarotene.

Figure 4:
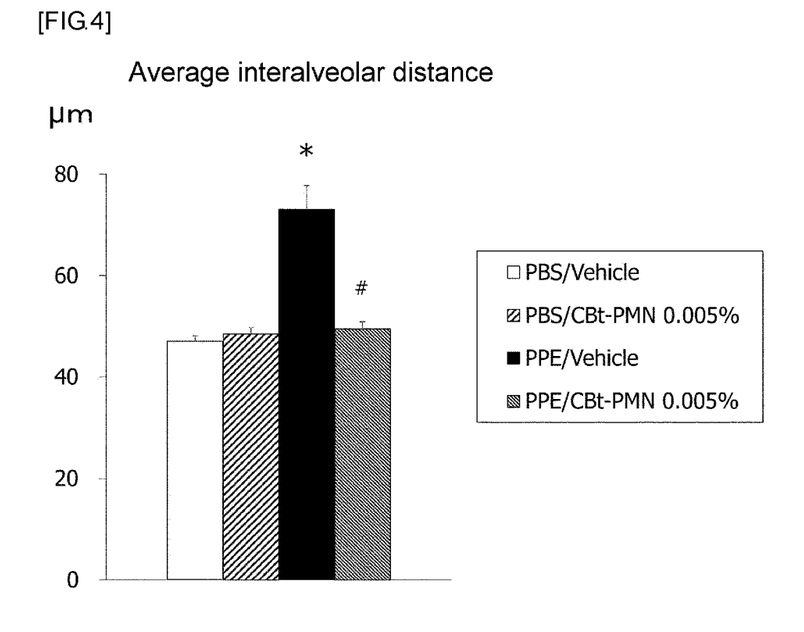
FIG. 4 is a graph for evaluating an average interalveolar distance in a lung tissue of emphysema model mice administered with CBt-PMN.
Figure 5:
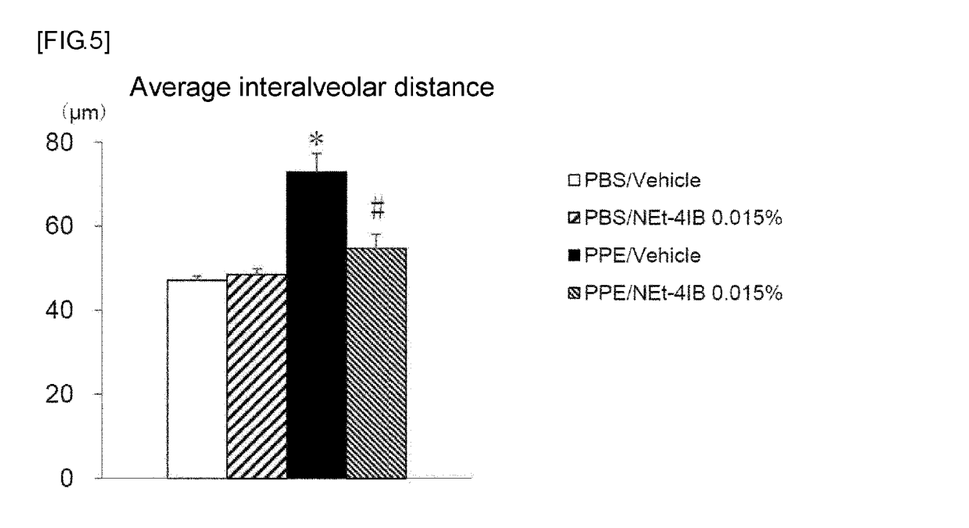
FIG. 5 is a graph for evaluating an average interalveolar distance in a lung tissue of emphysema model mice administered with NEt-4IB.
Figure 6:
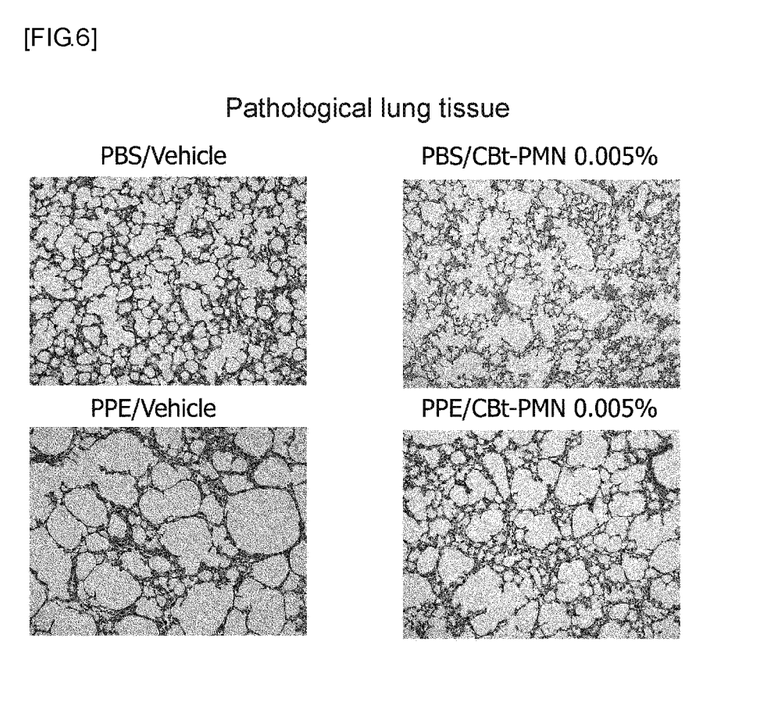
FIG. 6 is photographic images of HE staining of a lung tissue of emphysema model mice.

FIG. 4 is a graph for evaluating an average interalveolar distance in a lung tissue of emphysema model mice administered with CBt-PMN. FIG. 5 is a graph for evaluating an average interalveolar distance in a lung tissue of emphysema model mice administered with NEt-4IB. The lung tissue was fixed with formalin and then HE-stained, and an average interalveolar distance was determined for emphysema evaluation. Compared with the untreated group, improvement in emphysematous alteration was observed in the groups administered with an RXR partial agonist, CBt-PMN or NEt-4IB. Improvement was larger in the group administered with CBt-PMN than in the group administered with NEt-4IB. FIG. 6 shows photographic images of HE staining of a lung tissue of emphysema model mice. In the emphysema mice (PPE/Vehicle), enlargement of an alveolar space was observed in comparison with the non-disease-induction group (PBS/vehicle). In histopathological investigation of the lung tissue, significant improvement in enlargement of an alveolar space was observed in the group administered with the RXR partial agonist, CBt-PMN (PPE/CBt-PMN) in comparison with the untreated group (PPE/Vehicle).

Example 2

<Preparation of Bronchial Asthma Mice and Evaluation of Drug Efficacy>

Bronchial asthma mice were prepared and used for evaluation of drug efficacy in accordance with the following procedures.

[Procedure 1]

Female BALB/c mice were systemically sensitized by intraperitoneal administration of ovalbumin (OVA) (20 g of OVA emulsified in 2.25 mg aluminum hydroxide in a total volume of 100 μL) on Day 0 and Day 14, and then was exposed to inhaled OVA by an ultrasonic nebulizer (for 20 min, 3 days: Days 28 to 30), to induce asthma reaction.

[Procedure 2]

From Day 25, the mice were fed with a food containing an RXR agonist (NEt-4IB). On Day 32, the mice underwent tracheotomy under anesthesia by pentobarbital administration, followed by insertion of an endotracheal tube. After the tube was connected to a respiratory function measuring equipment, an airway hyperreactivity (airway resistance) was determined for evaluating airway constriction.

[Procedure 3]

Forty eight hours after the last OVA inhalation exposure, airway hyperreactivity in the mice with an endotracheal tube was measured using a respiratory function measuring equipment (Flexivent, SIREQ Inc.). Here, airway hyperreactivity was induced by inhalation of methacholine.

[Procedure 4]

After the procedure 2, the mice were euthanized by exsanguination. After bronchoalveolar lavage, a lung tissue was removed for evaluating an airway tissue.

[Procedure 5]

Also, for a group fed with a common food as an untreated group, an asthma reaction was induced in the same way for determination of airway hyperreactivity and evaluation of airway inflammation.

[Procedure 6]

Two groups which were not sensitized by an OVA and only exposed to inhaled OVA as non-asthma control groups (an RXR agonist medicated feed group and a common feed group) were also evaluated for airway hyperreactivity and airway inflammation in the same way.

[Procedure 7]

The data obtained was analyzed by Anova significance test, in which $p<0.01$ and $p<0.05$ to an untreated non-asthma group were indicated by "**" and "*", respectively. Furthermore, $P<0.05$ to an untreated asthma group was indicated by "#".

Figure 7:
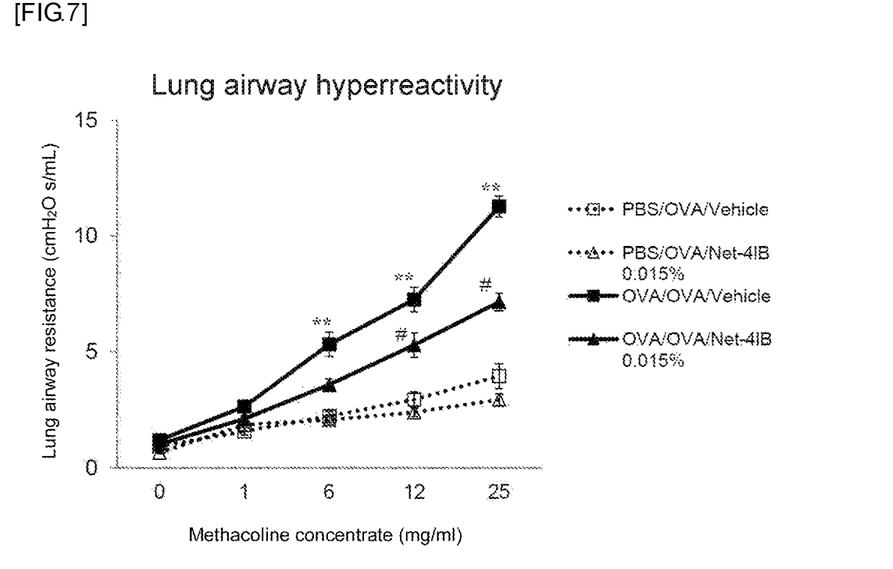
FIG. 7 is a graph for evaluating lung airway hyperreactivity in bronchial asthma model mice.

The results obtained are shown in FIGS. 7 to 10. FIG. 7 is a graph for evaluating lung airway hyperreactivity in bronchial asthma model mice. In the asthma mice, increase in an airway resistance was observed as a methacholine inhalation concentration increased. Compared with the untreated group indicated by black boxes (■), significant improvement in airway hyperreactivity was observed in the group administered with RXR partial agonist indicated by black triangles (▲).

Figure 8:
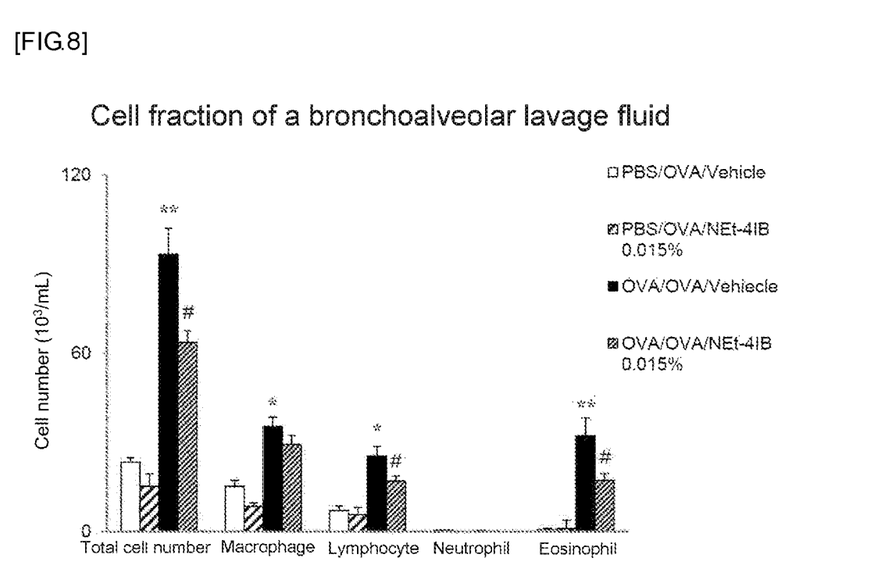
FIG. 8 is a graph of cell numbers in a cell fraction of a bronchoalveolar lavage fluid for bronchial asthma model mice.

FIG. 8 is a graph of cell numbers in a cell fraction of a bronchoalveolar lavage fluid for bronchial asthma model mice. Compared with the untreated group, reduction in a total cell number, a lymphocyte number and an eosinophil number was observed in the group administered with RXR partial agonist NEt-4IB.

Figure 9:
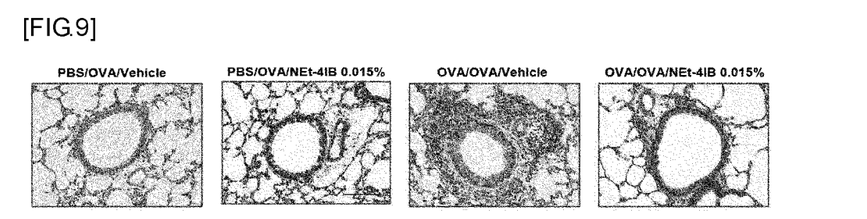
FIG. 9 is photographic images of HE staining of a lung tissue of bronchial asthma model mice.

FIG. 9 is photographic images of HE staining of a lung tissue of bronchial asthma model mice. The lung tissue was fixed with formalin and then HE-stained. In the OVA-sensitized mice, inflammatory cell infiltration mainly by eosinophils caused by inhalation exposure to the OVA was observed around vessel/airway in the pathological lung tissue. In histopathological investigation of the lung tissue, improvement in inflammatory cell infiltration in a local site of the airway was observed in the RXR partial agonist NEt-4IB administration group in comparison with the untreated group.

Figure 10:
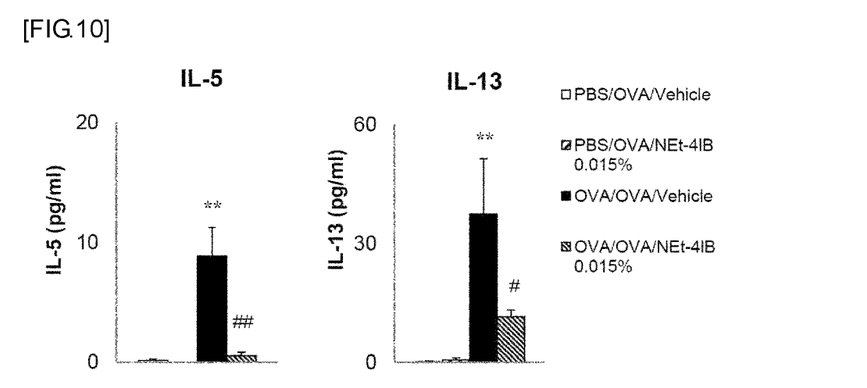
FIG. 10 is graphs of the results of determining cytokines (IL-5, IL-13) in a supernatant of a bronchoalveolar lavage fluid of bronchial asthma model mice.

FIG. 10 is graphs of the results of determining cytokines (IL-5, IL-13) in a supernatant of a bronchoalveolar lavage fluid of bronchial asthma model mice. Here, a supernatant in a bronchoalveolar lavage fluid was collected and cytokines were measured by ELISA method. Compared with the untreated group, inhibition of IL-5 and IL-13 as Th2 cytokines was observed in the RXR partial agonist NEt-4IB administration group.

All of the animal experiments were performed under the approval of the Animal Care and Use Committee, Okayama University.

As illustrated by the examples, CBt-PMN and NEt-4IB as RXR partial agonists exhibited significant anti-inflammatory effect in an emphysema model or a bronchial asthma model by repeated oral administration. As described above, the composition of the present invention can be expected to act as an active ingredient for preventing or treating an inflammatory respiratory disease, providing a useful medicinal drug.

The invention claimed is:

1. A method for treating an inflammatory respiratory disease, comprising administering an effective amount of RXR agonist as an active ingredient, wherein the inflammatory respiratory disease is emphysema or bronchial asthma wherein the RXR agonist is a compound represented by Formula (1)

wherein D is selected cMe$_2$, N-ethyl N-isopropyl;
R$^1$ is selected from a methyl group, a hydroxy group, a methoxy group or an ethoxy group,
R$^2$ is selected from H, a methyl group or an ethyl group;
X is selected from N, CH or C—CF$_3$,
Y is selected from N or CH;
Z is CH.

2. The method as claimed in claim 1, wherein the RXR agonist is a compound represented by Formula (3):

wherein X is selected from N or C—CF$_3$.

3. The method as claimed in claim 1, wherein the inflammatory respiratory disease is emphysema.

4. The method as claimed in claim 1, wherein the inflammatory respiratory disease is bronchial asthma.

5. The method as claimed in claim 1, wherein X is N, and Y is N.

6. The method as claimed in claim 5, wherein the inflammatory respiratory disease is emphysema.

7. The method as claimed in claim 5, wherein the inflammatory respiratory disease is bronchial asthma.

8. The method as claimed in claim 1, wherein the RXR agonist is a compound represented by Formula (1):

wherein D is selected from CMe$_2$, N-methyl, N-ethyl or N-isopropyl;
R$^1$ is selected from a methyl group, a hydroxy group, a methoxy group or an ethoxy group;
R$^2$ is selected from H, a methyl group or an ethyl group;
X is N;
Y is selected from N or CH;
Z is CH.

9. The method as claimed in claim 1, wherein the RXR agonist is a compound represented by Formula (1a):

(1a)

wherein D is selected from $CMe_2$, N-methyl, N-ethyl or N-isopropyl;
$R^1$ is selected from a methyl group, a hydroxy group, a methoxy group or an ethoxy group;
$R^2$ is selected from H, a methyl group or an ethyl group;
X is selected from CH or C—$CF_3$;
Y is selected from N or CH;
Z is CH.

10. The method as claimed in claim 1, wherein the RXR agonist is a compound represented by Formula (1b):

(1b)

wherein D is selected from $CMe_2$, N-methyl, N-ethyl or N-isopropyl;
$R^1$ is selected from a methyl group, a hydroxy group, a methoxy group or an ethoxy group;
$R^2$ is selected from H, a methyl group or an ethyl group;
X is selected from N, CH or C—$CF_3$;
Y is N;
Z is CH.

11. The method as claimed in claim 1, wherein the RXR agonist is a compound represented by Formula (1c):

(1c)

wherein D is selected from $CMe_2$, N-methyl, N-ethyl or N-isopropyl;
$R^1$ is selected from a methyl group, a hydroxy group, a methoxy group or an ethoxy group;
$R^2$ is selected from H, a methyl group or an ethyl group;
X is selected from N, CH or C—$CF_3$;
Y is CH;
Z is CH.

* * * * *

UNITED STATES PATENT AND TRADEMARK OFFICE
CERTIFICATE OF CORRECTION

PATENT NO.         : 11,026,932 B2
APPLICATION NO.    : 15/772901
DATED              : June 8, 2021
INVENTOR(S)        : Kanehiro et al.

Page 1 of 1

It is certified that error appears in the above-identified patent and that said Letters Patent is hereby corrected as shown below:

In the Claims

Column 11, Line 65 to Column 12, Line 4:
"wherein D is selected $cMe_2$, N-ethyl N-isopropyl;
  $R^1$ is selected from a methyl group, a hydroxy group, a methoxy group or an ethoxy group,
  $R^2$ is selected from H, a methyl group or an ethyl group;
  X is selected from N, CH or C-$CF_3$,
  Y is selected from N or CH;
  Z is CH."

Should read:
-- **wherein D is selected from $CMe_2$, N-methyl, N-ethyl or N-isopropyl;
  $R^1$ is selected from a methyl group, a hydroxy group, a methoxy group or an ethoxy group;
  $R^2$ is selected from H, a methyl group or an ethyl group;
  X is selected from N, CH, or C-$CF_3$;
  Y is selected from N or CH;
  Z is CH. --**

Signed and Sealed this
Fourth Day of January, 2022

Drew Hirshfeld
*Performing the Functions and Duties of the
Under Secretary of Commerce for Intellectual Property and
Director of the United States Patent and Trademark Office*